United States Patent [19]

Eaton

[11] Patent Number: 5,068,490

[45] Date of Patent: Nov. 26, 1991

[54] BF3-TERTIARY ETHERATE COMPLEXES FOR ISOBUTYLENE POLYMERIZATION

[75] Inventor: Bruce E. Eaton, Naperville, Ill.

[73] Assignee: Amoco Corporation, Chicago, Ill.

[21] Appl. No.: 534,696

[22] Filed: Jun. 6, 1990

Related U.S. Application Data

[63] Continuation of Ser. No. 396,380, Aug. 18, 1989, abandoned, which is a continuation of Ser. No. 162,046, Feb. 29, 1988, abandoned.

[51] Int. Cl.$^5$ ................................ C07C 2/08
[52] U.S. Cl. .................... 585/525; 423/293; 502/203
[58] Field of Search ............. 585/525; 423/293; 502/203

[56] References Cited

U.S. PATENT DOCUMENTS

| | | | |
|---|---|---|---|
| 2,384,916 | 9/1945 | Holmes | 260/93 |
| 2,559,062 | 7/1951 | Dornte | 260/93.5 |
| 2,559,984 | 7/1951 | Montgomery et al. | 260/683.15 |
| 2,588,425 | 3/1952 | Stevens et al. | 260/683.15 |
| 2,777,890 | 1/1957 | Ikeda | 260/680 |
| 2,780,664 | 2/1957 | Serniuk | 260/683.15 |
| 3,006,906 | 10/1961 | Geiser | 260/94.8 |
| 3,962,375 | 6/1976 | Throckmorton | 526/335 |
| 4,098,983 | 7/1978 | Osborn et al. | 585/525 |
| 4,152,499 | 5/1979 | Boerzel et al. | 526/52.4 |
| 4,849,572 | 7/1989 | Chen et al. | 585/525 |

FOREIGN PATENT DOCUMENTS 576759  5/1959  Canada .
804070  11/1958  United Kingdom .

*Primary Examiner*—Asok Pal
*Attorney, Agent, or Firm*—Reed F. Riley; William H. Magidson; Ralph C. Medhurst

[57] ABSTRACT

Disclosed herein are boron trifluoride etherate complexes in which the ether of the complex has at least one tertiary carbon bonded to an ether oxygen. The etherates are useful for polymerizing a one-olefin or mixtures thereof, preferably comprising isobutylene, whereby the resulting polymer contains a high percentage (80-100%) vinylidene character.

10 Claims, No Drawings

BF3-TERTIARY ETHERATE COMPLEXES FOR ISOBUTYLENE POLYMERIZATION

This is a continuation of application Ser. No. 396,380, filed Aug. 18, 1989, which is a continuation of U.S. Ser. No. 162,046, filed Feb. 29, 1988, now both abandoned.

FIELD OF THE INVENTION

The present invention relates generally to $BF_3$-etherate complexes useful for polymerization of 1-olefin containing feedstocks. More particularly the invention is directed to $BF_3$-etherates in which the ether of the $BF_3$-etherate has at least one tertiary carbon bonded to an ether oxygen, and to a process for polymerizing feedstocks comprising isobutylene wherein the $BF_3$-tertiary etherate is the catalyst. The $BF_3$-tertiary etherates of the present invention and the polymerization process employing them are suitable for manufacturing polybutene having a very high percentage (80 to 100%) of vinylidene olefin.

DISCUSSION OF THE PRIOR ART

Generally speaking, polymerization of 1-olefin containing feedstocks using catalysts such as aluminum chloride and boron trifluoride is disclosed extensively in the patent and technical literature. It is well known that the termination step in isobutylene polymerization results in a "terminal" double bond which imparts desired reactivity to the polymer for subsequent reactions, such as epoxidization or reaction with maleic anhydride. However, a problem exists in that the termination step can place the terminal double bond in a highly reactive external 1,1-disubstituted position (hereafter "vinylidene"), or in a much less reactive internal tri-substituted or tetrasubstituted position. These three possible terminal double bond positions are shown below.

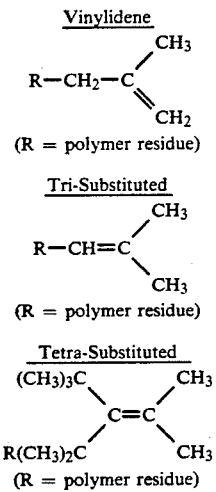

Vinylidene
(R = polymer residue)

Tri-Substituted
(R = polymer residue)

Tetra-Substituted
(R = polymer residue)

Referring to this problem, Samson U.S. Pat. No. 4,605,808 states that the product obtained upon conventional polymerization of isobutylene is generally a mixture of polymers having a high proportion of internal versus external (vinylidene) unsaturation due to "in situ" isomerization of the more highly reactive vinylidene double bond to the less reactive internal positions. The diminished reactivity of the hindered internal tri-substituted or tetra-substituted double bond is most notably observed in the manufacture of the valuable intermediate polyisobutenyl succinic anhydride ("PIBSA") which is obtained by reaction of maleic anhydride with polybutene. PIBSA is a very important intermediate in the manufacture of fuel and lubricant additives. The lowered reactivity of polybutene due to the presence of substantial internal olefinicity reduces the yield of PIBSA when the polymer is reacted with maleic anhydride and thus dictates higher usage of polybutene than would otherwise suffice if the polybutene consisted mainly of vinylidene olefin.

Given the above problem, it has long been an object of research in the area of polybutene manufacture to improve the reactivity of polybutene, particularly its reactivity toward maleic anhydride, by identifying catalysts or catalyst systems capable of polymerizing isobutylene such that the resulting polybutene has the highest possible percentage of vinylidene double bonds.

A number of patents have sought to address this very problem. Nolan U.S. Pat. No. 3,166,546 discloses a vapor phase process for isobutylene polymerization which requires using a mixture of gaseous boron trifluoride and sulfur dioxide under specified conditions. The patent states that sulfur dioxide directs the polymerization reaction such that substantially all of the polybutene has vinylidene unsaturation. In column 1 of the patent, it is stated that the boron trifluoride catalyst requires a small amount of water, alcohol, carboxylic acid, mineral acid or ether to initiate the catalyst. However, there is no suggestion for the use of $BF_3$-tertiary etherate complexes. Moreover, the sulfur dioxide process does not appear to be commercially viable.

In later work using $BF_3$ catalyst, Boerzel et al. U.S. Pat. No. 4,152,499 disclosed that $BF_3$ mainly favors the formation of polymer having the reactive double bond in the vinylidene position if a short polymerization time (3 to 5 minutes) is strictly maintained.

Most recently, Samson U.S. Pat. No. 4,605,808 discloses isobutylene polymerization using a preformed boron trifluoride/alcohol complex and contact times in the range of 8 to 70 minutes, as a means of obtaining a high percentage (at least 70 percent) of vinylidene content in the resulting polybutene polymer.

While the patents cited above dealing with $BF_3$ catalysis are indicative of progress toward the achievement of a highly reactive (high vinylidene) polybutene, a number of problems remain to be solved. First, the teachings of these patents place strict restraints on the contact time for the catalysts. For example, in the case of the above cited Boerzel Patent, a contact time of 1 to 10 minutes is claimed but 3 to 5 minutes is the preferred range. If the brief contact times are not maintained, the desired high levels of vinylidene unsaturation cannot be achieved given the tendency of the vinylidene double bonds in the polymer to isomerize in the presence of the catalyst to the less reactive internal type double bond.

To some extent, this problem may have been alleviated in the Samson '808 patent teaching use of a preformed boron trifluoride/alcohol complex with contact times of 8 to 70 minutes to obtain polymer having at least 70% vinylidene content. Nevertheless, it is desired to increase even further the percentage of vinylidene content obtainable in the polymer, while at the same time eliminating or minimizing the dependency of such outcome upon rigorously maintained contact times.

Inasmuch as the present invention relates generally to isobutylene polymerization in the presence of boron trifluoride etherate complexes, a number of additional literature references and patents, in addition to those already discussed above, are believed to be of general relevance although they fail to address the problem sought to be overcome by the present invention and can be readily distinguished. For example, Dornte U.S. Pat. No. 2,559,062 discloses isobutylene polymerization using boron trifluoride complexed with di-n-butyl ether, halogen-substituted dialkyl ethers, aryl-alkyl mixed ethers, nitroaryl ethers, cyclic ethers and unsaturated ethers. The patent notes that the types of ethers used for complexation with BF$_3$ may not be indiscriminately selected, and makes no mention of tertiary etherates in which a tertiary carbon is bonded to the ether oxygen.

Stevens et al. U.S. Pat. Nos. 2,588,425 and 2,591,384 disclose preparation of an isobutylene polymer consisting almost exclusively of tetraisobutylene or triisobutylene. The tetramer or trimer is prepared from isobutylene at 0° C. to 55° C. in the presence of a boron trifluoride ether complex. The ether compounds disclosed by Stevens do not include tertiary ethers.

Montgomery et al. U.S. Pat. No. 2,559,984 teach the use of aluminum chloride or boron fluoride catalysts complexed with organic compounds, but the patent mentions ethers only in the context of aluminum chloride catalysts.

Ikida U.S. Pat. No. 2,777,890 discloses the use of a boron trifluoride diethylether complex as a catalyst for polymerization of butadiene-1,3.

Throckmorton U.S. Pat. No. 3,962,375 discloses boron trifluoride complexed with ethers of the formula ROR' where R and R' represent alkyl, cycloalkyl, aryl, alkyaryl, arylalkyl radicals containing from 1 to about 30 carbons.

Serniuk U.S. Pat. No. 2,780,664 discloses preparation of a drying oil by contacting a mixture of 75 parts by weight of butadiene and 25 parts by weight of isobutylene in the presence of boron trifluoride ethylether complex.

Geiser U.S. Pat. No. 3,006,906 discloses copolymerization of isobutylene with a tetra-substituted alkylene diamine in the presence of a boron trifluoride ethylether complex.

Holmes U.S. Pat. No. 2,384,916 discloses a method of producing high molecular weight iso-olefin polymers using boron trifluoride catalysts promoted with ethylether, normal propylether, isopropylether, normal butylether, methyl normal butylether and isomaylether. The use of boron trifluoride:tertiary ether complexes to obtain polybutene having high levels of vinylidene unsaturation is no where disclosed or suggested in this patent.

Finally, it should be noted that early work by Evans et al. determined the necessity in BF$_3$ catalysis of a complexing agent able to donate a proton. Evans discovered that no polymerization will occur when pure diisobutylene is exposed to BF$_3$ unless a trace amount of moisture is present. This finding has generally led to the acceptance of a cationic mechanism, and therefore the requirement of a proton source, for both BF$_3$ and AlCl$_3$ catalysis. The early work of Evans in conjunction with his associates, Meadows and Polanyi, is described in Nature (1947) 160, page 869; J. Chem. Soc. (1947) 252; and Nature (1946) 158, page 94. To date, the cationic mechanism ascribed to BF$_3$ and AlCl$_3$ catalysis requiring proton donation to initiate polymerization is widely accepted.

To the best of my knowledge the patents and literature references discussed above with respect to the use of BF$_3$-etherate complexes are not addressed to the attainment of high vinylidene content in polybutene and do not teach tertiary etherates capable of achieving that result. On the contrary the BF$_3$ ether complexes taught in these early patents are inactive unless they are activated with a proton source. Under the accepted cationic mechanism for such polymerization the actual BF$_3$ catalyst in the presence of such a proton source acts as a Lewis acid having a strong tendency to isomerize the vinylidene double bonds to the less reactive internal double bonds and to cause skeletal rearrangements and branching of the polybutene formed during the polymerization reaction. The latter is a disadvantage in that a highly linear polymer is generally preferred in lubricant additive manufacture.

In view of the foregoing discussion of the prior art, an object of the present invention is generally to provide an improved BF$_3$ catalyst system useful in the preparation of polybutene having a high percentage of vinylidene unsaturation. Other objects will be apparent hereinafter to those skilled in the art.

SUMMARY OF THE INVENTION

I have now discovered an improved boron trifluoride catalyst system for use in the polymerization of 1-olefin containing feedstocks. The catalyst system comprises a BF$_3$-etherate complex in which the ether has at least one tertiary carbon bonded to an ether oxygen. The tertiary ether can have the general formula:

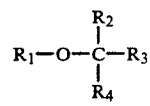

where R$_1$ is C$_1$ to C$_{20}$ hydrocarbyl or halo-substituted hydrocarbyl and R$_2$, R$_3$ and R$_4$, the same or different, are selected from the group consisting of (1)—CH$_2$R' where R' is H, halogen, or C$_1$ to C$_{20}$ hydrocarbyl or halo substituted hydrocarbyl; (2)—CH=R'' where R'' is C$_1$ to C$_{20}$ hydrocarbyl or halo substituted hydrocarbyl; and (3)—C≡R''' where R''' is C$_1$ to C$_{20}$ hydrocarbyl or halo substituted hydrocarbyl. Preferred tertiary ethers for use in preparation of the BF$_3$-etherate complexes of the present invention are those in which R$_2$, R$_3$ and R$_4$ in the above formula are methyl, and R$_1$ is C$_1$ to C$_{10}$ hydrocarbyl. Particularly preferred are the alkyl tert-butyl ethers, e.g., methyl t-butyl ether, n-butyl t-butyl ether, isopropyl t-butyl ether, di-tert-butyl ether, ethyl tert-butyl ether, pentyl tert-butyl-ether, 1,1'-dimethylbutyl methylether, etc.

As a method, the present invention is directed to a process for polymerizing a feedstock comprising 1-olefin which process comprises the step of contacting the feedstock with a BF$_3$-tertiary etherate as described above at −100° to +50° C. The process is suitable for polymerizing isobutylene to obtain commercial grade polybutene having high percentages of vinylidene olefinicity (i.e., 80 to 100%).

A principle advantage of the BF$_3$-tertiary etherate complexes of the present invention is their ability to produce polybutene polymer having higher percentages of vinylidene unsaturation (80 to 100%) than obtained using the BF$_3$-catalysts of the prior art (i.e., Boerzel U.S. Pat. No. 4,152,499 and Samson U.S. Pat. No. 4,605,808) which, by comparison, are taught to be capable of producing vinylidene contents in the range of only about 60 to 90%.

The etherates of the present invention also compare favorably to the $BF_3$-alcoholate complexes of Samson in their ability to produce higher molecular weight polymer at a given temperature.

Still a further advantage is that longer residence times are acceptable in the $BF_3$-etherate catalyzed polymerization of the present invention. Residence times of 10 minutes to 3 hours (or greater) can be used depending upon temperature, catalyst concentration and desired molecular weight.

Further advantages include the fact that the $BF_3$-etherates of the present invention are more active than $BF_3$-alcohol complexes and show greater selectivity for isobutylene than conventional $AlCl_3$ catalyst. This latter advantage reduces the stripping required for the raw polybutene product.

Finally, in comparison to aluminum chloride catalyzed polymerization, the polybutene product resulting from the $BF_3$-tertiary etherates of the present invention is more linear (less branching and skeletal rearrangements) and is consistently colorless.

Surprisingly, unlike the prior art $BF_3$ catalyst systems which require a protic source (i.e., water, alcohol, mineral acid, etc.) to initiate polymerization, the $BF_3$-tertiary etherate complexes of the present invention do not require protic initiation. In fact, they are found to perform optimally in terms of high vinylidene content, using feeds that are essentially completely free of water or other protic species capable of complexing with the $BF_3$ by displacement of the tertiary ether. As the presence of water or other proton donating species in the feed or reaction zone increases, even slightly, the ability of the $BF_3$-tertiary etherates to produce high vinylidene falls off dramatically. Therefore the preferred feedstock for use in the present invention should be as anhydrous as possible, preferably containing no greater than about 1 to about 10 ppm water. However feeds having 10 to 20 ppm $H_2O$ can be used without seriously impairing the advantages of the present invention. At levels greater than about 20 ppm $H_2O$, the $BF_3$ etherates of the present invention may perform worse than the prior art $BF_3$ catalysts measured in terms of the ability to produce high vinylidene content in the polymer product.

Without any intention to be bound to a particular theory, it is believed that the advantages noted above, namely higher vinylidene content, longer residence times, higher molecular weight polymer, more linear polymer, etc., result from the fact that the $BF_3$ tertiary etherates of the present invention do not require protic initiation for polymerization to take place. Protic initiation, characteristic of a cationic mechanism for isobutylene polymerization results in a reaction environment which is highly acidic due to the proton donation by the active catalyst species, such active species being a complex of the protonic entity (for example water) and the $BF_3$. The acidic reaction environment characteristic of proton initiated polymerization is believed the principle cause underlying isomerization of terminal vinylidene unsaturation to the less desired and less reactive internal unsaturation. Acidity at the onset of polymerization resulting from proton donation of the catalyst species also causes skeletal rearrangements and fragmentation of the forming polybutene polymer. By comparison, in view of the evidence that the $BF_3$ tertiary etherate complexes of the present invention are capable of operating in an essentially completely anhydrous environment requiring no protic initiation, polymerization in accordance with the present invention is initiated in a substantially nonacidic environment which reduces acid catalyzed isomerization of vinylidene double bonds to di-, tri- and tetra-substituted internal double bonds. Also, fragmentation and skeletal rearrangements are minimized. As distinguished from a cationic mechanism, it is believed that polymerization in the present invention proceeds via a covalent mechanism.

A critical feature of the present invention which dictates the ability of the $BF_3$-etherates disclosed herein to produce high vinylidene polymer and to operate without necessity of protic initiation, is that the ether in the $BF_3$-etherate complexes must have at least one tertiary carbon bonded to the ether oxygen. $BF_3$-etherates which do not fulfill this requirement are outside the scope of the present invention and will not polymerize isobutylene in such a manner as to produce the very high levels of vinylidene possible in the present invention.

DETAILED DESCRIPTION

The $BF_3$-tertiary etherates of the present invention can be prepared by reacting gaseous $BF_3$ with a tertiary ether under carefully controlled conditions of temperature and rate of reaction whereby the exothermicity of the $BF_3$-etherate complex formation is prevented from causing the decomposition of the complex. In the case of the $BF_3$-methyl t-butyl ether or n-butyl t-butyl ether complexes, such decomposition would result in the formation of $BF_3$ methanol (or butanol) complexes with the release of isobutylene and dimers or trimers of isobutylene. To prevent such decomposition, gaseous $BF_3$ can be bubbled into the ether at a relatively slow rate over a period of about 1 to 5 hours and at a temperature not exceeding about 0° C. A preferred temperature to minimize breakdown of the etherate complex is about $-60°$ to about $-30°$ C. If desired, a further means of controlling the reaction between the $BF_3$ and the ether is to dilute the $BF_3$ with an inert gas such as nitrogen and/or dilute the ether with inert solvents such as dichloromethane.

Ether having a tertiary carbon bonded to the ether oxygen can be used in the preparation of the $BF_3$-etherates of the present invention. Suitable ethers include methyl tertiary-butyl ether, ethyl tertiary-butyl ether, n-propyl tertiary-butyl ether, isopropyl tertiary-butyl ether, ditertiary-butyl ether, 1,1'-dimethylbutyl methyl ether, and so on. The tertiary position of the ether is preferably a tertiary butyl group for smoothest initiation of polymerization and minimization of branching or skeletal rearrangement in isobutylene polymerization. Also, generally speaking, as the hydrocarbyl group (preferably alkyl) of the non-tertiary portion of the ether is increased from methyl to isopropyl to butyl, etc., the molecular weight of the resultant polybutene polymer is increased.

The mole ratio of ether to $BF_3$ in the etherates of the present invention should be in the range of about 0.5 to about 3:1. Preferably, to maximize attainment of high vinylidene content in the resulting polybutene polymer, the ether should be in at least a slight molar excess of the $BF_3$, most preferably in the range of about 1:1 to about 1.1:1. At mole ratios below about 1:1, the vinylidene content begins to decrease. Above about 1.1:1 little further improvement is observed.

The $BF_3$-etherates can be prepared ahead of time for subsequent use as a preformed catalyst complex, such as when polymerization is to be carried out in a batch process. In a continuous process the BF$_3$-etherates can be preformed in line immediately prior to entering the polymerization reaction. If performed ahead of time and stored for subsequent use, the BF$_3$ etherates should be maintained at 0° C. or less to prevent decomposition.

The present invention is also directed to a process for polymerizing a feedstock comprising 1-olefins which process comprises contacting the feedstock with the BF$_3$-tertiary etherates described above.

The hydrocarbon feedstock may be pure 1-olefin or a mixture of 1-olefins. 1-olefin feedstock where the olefin contains 3 to 16 carbon atoms is preferred. If a pure olefin is used which is gaseous under ambient conditions it is necessary either to control the reaction pressure or to dissolve the olefin in a solvent medium inert under the reaction conditions in order to maintain the olefin in the liquid phase. In the case of isobutylene, which is typical of 1-olefins, the feedstock used in the polymerization process may be pure isobutylene or a mixed C$_4$ hydrocarbon feedstock such as that resulting from the thermal or catalytic cracking operation conventionally known as a butadiene or C$_4$ raffinate. This is a liquid when under pressure and hence no diluent is needed. The feedstock used may suitably contain between 5 and 100% by weight of isobutylene. It is preferred to use a feedstock containing at least about 10% by weight of isobutylene. The hydrocarbon feedstock used may contain, in addition to isobutylene, butanes and butenes without adverse effect on the polybutene product.

The polymerization temperature should be selected based on the molecular weight desired in the product. As is well known, lower temperatures can be used for higher molecular weights while higher temperatures can be used to obtain lighter products. The polymerization of the present invention can be carried out in the full range of temperatures generally associated with conventional polybutene polymerization, i.e., about −100° C. to about +50° C. Polybutene molecular weights in the greatest commercial demand, i.e., those of molecular weight 100 to about 5000 can be obtained in the polymerization of the present invention at temperatures in the range of about −50° C. to about +10° C.

The residence time required in the polymerization of the present invention represents an important advantage over the prior art which generally teaches short, strictly controlled residence times. For example, in Boerzel U.S. Pat. No. 4,152,499, it is shown that residence times exceeding about 10 minutes are detrimental to the vinylidene character of the polymer. By comparison, typical residence times in the present invention range from about 10 minutes to 3 hours, while residence times of greater than 3 hours can be used to produce heavy polymer in reactions carried out at very low temperatures (i.e., −30° to −100° C.). Such longer residence times are possible without the adverse effects upon vinylidene content noted in column 1 of the Boerzel '499 patent. Generally speaking, while the choice of residence time will be dictated in a known manner by factors such as the isobutylene concentration in the feed, temperature of reaction, catalyst concentration and the desired molecular weight of the product, it should be pointed out that the residence time should not be allowed to extend longer than the time required for the isobutylene concentration in the feed to decrease to about 1 wt % (which can be readily monitored by gas chromatography). If allowed to continue beyond this point, the polymer is susceptible to isomerization of the desired vinylidene double bond to the less reactive trior tetra-substituted internal double bond.

The amount of BF$_3$-etherate used in the polymerization is not critical to the invention. Generally speaking, amounts ranging from at least about 0.01 mole percent based on isobutylene in the feed are suitable. About 0.05 to about 1 mole % is sufficient to obtain conversions of isobutylene of 80–90%. Generally speaking, raffinate feeds may require higher levels of the BF$_3$ complex than would suffice for a feed of pure isobutylene, to obtain 80–90% conversions. This is believed due to the number of competing reactions in the raffinate as opposed to synthetic feeds.

The polymerization of the present invention aided by the novel BF$_3$-tertiary etherates disclosed herein can be used to obtain a full range of polybutene molecular weights depending upon conditions of reaction time, feed, reaction temperature, etc. all of which can be controlled in a known manner. Polybutene obtained from the present invention having 80 to 100% vinylidene is more reactive than conventional polybutene having much lower vinylidene. As such the polybutene prepared in the present invention is particularly well suited for reaction with maleic anhydride to obtain valuable PIBSA intermediates useful in the manufacture of fuels and lubricant additives.

The following examples are intended for illustration only and should not be construed as limiting the invention set forth in the claims.

EXAMPLE I

Preparation of BF3-Methyl-t-butyl Etherate

Into a 150 ml flask was charged 33 ml (0.28 moles) of methyl-t-butyl ether (MTBE). The flask of ether was then cooled to −40° C. Gaseous BF$_3$ (6610 cc; 0.28 moles) was then slowly bubbled into the ether at a rate of 22 cc/min. with vigorous stirring. The gas phase of the flask was continually purged with nitrogen and the vent gases bubbled through 20% NaOH to remove acidic components. After addition of the BF$_3$ was complete, the gas phase of the flask was purged for another 20 minutes to ensure removal of free BF$_3$. The BF$_3$-methyl t-butyl etherate was stored at 0° C. until ready for use.

EXAMPLE II

Example I was repeated except that ethyl-t-butyl ether was used instead of MTBE.

EXAMPLE III

Example I was repeated using n-butyl-t-butyl ether.

EXAMPLE IV

Example I was repeated using isopropyl-t-butyl ether.

EXAMPLE V

Example I was repeated using di-t-butyl ether.

EXAMPLE VI

Example I was repeated using n-propyl-t-butyl ether.

EXAMPLE VII

Example I was repeated using isoamyl-t-butyl ether.

EXAMPLE VIII

Example I was repeated using 1,1'-dimethylbutyl-methyl ether.

EXAMPLE IX

Example I was repeated using cyclohexyl-t-butyl ether.

EXAMPLE X

Example I was repeated using benzyl-t-butyl ether.

EXAMPLE XI

The $BF_3$-MTBE complex of Example I was used to polymerize a feed consisting of 20% isobutylene in isobutane. The feed contained less than 1.0 ppm water. Three separate batch polymerizations (summarized in Table 1 below) were run in an autoclave batch reactor equipped with a heat exchanger and in line cooling coils. The autoclave was cooled to the desired temperature followed by addition of 550 grams of the feed. The $BF_3$-MTBE complex was charged to a pre-cooled stainless steel bomb attached to the reactor inlet. The complex was introduced into the reactor by purging the bomb with 50 grams of the abovementioned feed, followed by nitrogen to obtain a pressure in the reactor of 200 psi. The reaction conditions for each run are summarized in the Table 1 below. Each run produced colorless polybutene having at least 80% vinylidene content. Product olefin distribution (i.e., relative amount of vinylidene, tri-substituted and tetra-substituted double bond) was determined by $^{13}C$ NMR.

TABLE 1

| Isobutylene Polymerization Using $BF_3$-MTBE | | | | |
|---|---|---|---|---|
| Reaction Temp (°C.) | Mole % of Catalyst* | % Isobutylene Conversion | Mn | Mw |
| 0 | 0.05 | 92 | 283 | 441 |
| 0 | 0.10 | 98 | 279 | 409 |
| 10 | 0.29 | 88 | 240 | 303 |

| Dispersion Index | $^{13}C$ NMR Analysis | | |
|---|---|---|---|
|  | % Vinylidene | % Tri | % Tetra |
| 1.56 | 80 | 17 | 3 |
| 1.59 | 81 | 16 | 3 |
| 1.26 | 81 | 16 | 3 |

*mole % of catalyst relative to isobutylene.

EXAMPLE XII

In a pilot plant continuous reactor cooled to $-15°$ C., $BF_3$-MTBE was preformed by in-line mixing of $BF_3$ and methyl-t-butyl ether just prior to entering the reactor. The mole ratio of ether to $BF_3$ was 1:1. The feed was a typical refinery $C_4$ raffinate (water washed and dried) containing 18% isobutylene and 5 ppm water. The catalyst load was 0.36 mole percent in relation to the washed feed. The colorless product (total polymer) had an olefin distribution of 74% vinylidene, 13% tri-substituted and 8% tetrasubstituted. The stripped polymer had 87% vinylidene, $M_n=626$, $M_w=789$, dispersion index=1.29 and a flash point (ASTM D-92 COC) of 242° C.

EXAMPLE XIII

The batch polymerization process outlined in Example XI was repeated except that $BF_3$-butyl-t-butyl etherate (Example II) was used instead of $BF_3$-MTBE. Table 2 below summarizes the reaction conditions and results for two separate runs. As in Example XI, the feed was 20% isobutylene in isobutane and virtually anhydrous (<1 ppm $H_2O$). Both runs were conducted at $-18°$ C. with a residence time of 60 minutes. The mole ratio of ether to $BF_3$ in the catalyst complex was 1.1:1.

TABLE 2

| Isobutylene Polymerization Using $BF_3$-BTBE | | | |
|---|---|---|---|
| Init. Conc.* of BTBE-$BF_3$ | GPC Data | | |
|  | Mn | Mw | DI |
| 0.13 | 1228 | 2631 | 2.14 |
| 0.13 | 1419 | 2756 | 1.94 |

*The concentration of BTBE-$BF_3$ in mole % relative to isobutylene.

| Olefin Distribution 13C NMR | | |
|---|---|---|
| % Vinylidene | % Trisubstituted | % Tetrasubstituted |
| 87 | 8 | 5 |
| 93 | 7 | 0 |

EXAMPLE XIV

The batch polymerization of Example XI was repeated except that $BF_3$-butyl-t-ether ($BF_3$-BTBE) was substituted for $BF_3$-MTBE, and a water washed (and dried) refinery $C_4$ raffinate was substituted for the 20% isobutylene in isobutane feed. Table 4 below summarizes the results of four separate runs. Each run was carried out at $-18°$ C. with a residence time of 40 minutes. Raffinate source "A" (Whiting) consisted of about 14% isobutylene and was dried to <5 ppm $H_2O$. Raffinate source "B" (Texas City) consisted of about 18% isobutylene and was dried to a moisture content of <5 ppm $H_2O$. The mole ratio of butyl-t-butyl ether to $BF_3$ in the complex was 1.1:1.

TABLE 3

| Isobutylene Polymerization Using $BF_3$:BTBE and C4 Raffinate | | | | |
|---|---|---|---|---|
| Raffinate Source | Mol % Catalyst | GPC Data | | |
|  |  | Mn | Mw | DI |
| A | 0.76 | 902 | 1534 | 1.70 |
| A | 1.01 | 916 | 1446 | 1.77 |
| B | 0.52 | 806 | 1842 | 2.29 |
| B | 0.78 | 569 | 1044 | 1.83 |

| Olefin Distribution 13C NMR | | |
|---|---|---|
| % Vinylidene | % Trisubstituted | % Tetrasubstituted |
| 84 | 12 | 4 |
| 80 | 17 | 3 |
| 81 | 14 | 5 |
| 80 | 15 | 5 |

EXAMPLE XV

Using the batch polymerization outlined in Example XI, with $BF_3$-BTBE catalyst, the effect on vinylidene content of varying the mole ratio of BTBE to $BF_3$ was studied in five separate runs summarized in Table 4 below. The feed was 20% isobutylene in isobutane (<1 ppm $H_2O$), the reaction temperature was $-18°$ C. and the residence time was 40 minutes.

TABLE 4

| Effect of Varying Mole Ratio of Ether to $BF_3$ Upon Vinylidene Content | | | | |
|---|---|---|---|---|
| Mole Ratio BTBE/$BF_3$ | Mol. % BTBE:$BF_3$ | Olefin Dist. $^{13}C$ NMR | | |
|  |  | Vinylidene | Tri | Tetra |
| 1:1 | 0.38 | 76 | 15 | 9 |

TABLE 4-continued

Effect of Varying Mole Ratio of Ether to BF3 Upon Vinylidene Content

| Mole Ratio BTBE/BF3 | Mol. % BTBE:BF3 | Olefin Dist. $^{13}$C NMR Vinylidene | Tri | Tetra |
|---|---|---|---|---|
| 1.1:1 | 0.52 | 83 | 17 | 0 |
| 1:1 | 0.38 | 75 | 18 | 8 |
| 0.8:1 | 0.52 | 63 | 30 | 7 |
| 1.1:1 | 0.62 | 83 | 15 | 2 |

TABLE XVI

The batch polymerization of Example XI was repeated except that the BF3 etherate was prepared from isopropyl-t-butyl ether (PTBE). The feed was 20% isobutylene in isobutene containing less than 1 ppm H2O. Five runs were carried out using a reaction temperature of 0° C. and a residence time of 50 minutes. The runs are summarized in Table 5 below.

TABLE 5

Isobutylene Polymerization Using BF3:PTBE

| Mole Ratio PTBE:BF3 | Mol % Catalyst | Mn | Mw | DI |
|---|---|---|---|---|
| 1.1:1 | 0.56 | 323 | 478 | 1.48 |
| 1:1 | 1.56 | 381 | 583 | 1.53 |
| 1.1:1 | 0.42 | 403 | 613 | 1.52 |
| 1.1:1 | 0.56 | 487 | 746 | 1.53 |
| 1:1 | 0.22 | 713 | 1272 | 1.78 |

| % Vinylidene | Olefin Distribution 13C NMR % Trisubstituted | % Tetrasubstituted |
|---|---|---|
| 100 | 1 | — |
| 85 | 13 | 2 |
| 100 | — | — |
| 100 | — | — |
| 85 | 11 | 4 |

EXAMPLE XVII

For purposes of comparison, BF3-ethanol and BF3-butanol complexes were evaluated for their ability to produce polybutene having high vinylidene content. BF3-ethanol and BF3-butanol complexes were prepared using the general procedures of Example I as follows: Into a flask was charged 1.09 moles of ethanol or butanol. The flask was then cooled to 0° C. with an ice bath. Gaseous BF3 (1.09 moles) was bubbled into the flask with vigorous stirring over a period of about 120 minutes. The gas phase of the reaction vessel was continually purged with nitrogen and the vent gases bubbled through 20% NaOH to remove acidic components. Following addition of all the BF3 the gas phase of the flask was purged with nitrogen for another 20 minutes to ensure removal of any free BF3. The resulting BF3 ethanol or butanol complexes were evaluated in a series of runs for polymerization of a feed consisting of 20% isobutylene in isobutane. In Table 6, below, the concentration of the BF3-alcohol complex was 0.19 mole % based on the feed, the reaction temperatures were varied (9° C-1° C. and —10° C.) and the residence times were as long as necessary to react about 99% of the isobutylene, which in all of the runs was about 20 minutes. The batch polymerizations were carried out according to the procedures outlined in Example XI. Table 6 below summarizes the results of 3 BF3-ethanol runs.

TABLE 6

Isobutylene Polymerization Using BF3-Ethanol Complex

| Reaction Temp. °C. | GPC Data Mw | Mn |
|---|---|---|
| 9 | 500 | 300 |
| —1 | 600 | 400 |
| —10 | 1000 | 600 |

| % Vinylidene | Olefin Distribution 13C NMR % Trisubstituted | % Tetrasubstituted |
|---|---|---|
| 76 | 22 | 2 |
| 73 | 24 | 3 |
| 80 | 17 | 3 |

A BF3-butanol complex as prepared above was evaluated in four batch polymerization runs using 20% isobutylene in isobutane as the feed. The catalyst concentration was 0.18 mole %, residence times (allowing for reaction of 99% of the isobutylene in the feed) were 30 minutes and the reaction temperatures were —18° C., —12° C., 0° and 10° C. Table 7 below summarizes these four BF3-butanol runs.

TABLE 7

Isobutylene Polymerization Using BF3-Butanol Complex

| Reaction Temp. °C. | GPC Data Mw | Mn |
|---|---|---|
| —18 | 1700 | 800 |
| —12 | 1400 | 700 |
| 0 | 800 | 400 |
| 10° | 450 | 300 |

| % Vinylidene | Olefin Distribution 13C NMR % Trisubstituted | % Tetrasubstituted |
|---|---|---|
| 75 | 18 | 7 |
| 72 | 21 | 7 |
| 72 | 22 | 6 |
| 72 | 23 | 5 |

I claim:

1. A process to form a product which is essentially polyisobutylene containing at least about 80 percent vinylidine, which process comprises polymerizing isobutylene or a mixed C4 hydrocarbon feedstock containing at least about 5 weight % isobutylene and up to 20 parts per million water with a boron trifluoride etherate complex wherein the ether of said complex has at least one tertiary carbon bonded to the ether oxygen.

2. The process of claim 1 wherein the boron trifluoride etherate has the general formula:

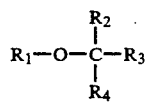

wherein $R_1$ is a $C_1$ to $C_{20}$ hydrocarbyl or halo-substituted hydrocarbyl and $R_2$, $R_3$, and $R_4$, being the same or different, are selected from the group consisting of (a) —CH$_2$R', where R' is H, halogen, or a $C_1$ to $C_{20}$ hydrocarbyl (b) —CH=R'', and (c) —C≡R''', wherein R'' and R''' are the same or different and R'' and R''' are selected from a $C_1$ to $C_{20}$ hydrocarbyl or halo-substituted hydrocarbyl.

3. The process of claim 2 wherein $R_2$, $R_3$ and $R_4$ are methyl.

4. The process of claim 3 wherein $R_1$ is selected from the group consisting of methyl, ethyl, propyl, isopropyl, butyl, isobutyl, t-butyl.

5. The process of claim 4 wherein $R_1$ is methyl.

6. The process of claim 5 wherein the etherate is the reaction product of the ether and boron trifluoride reacted in a mole ratio of at least about 1:1.

7. The process of claim 4 wherein $R_1$ is butyl.

8. The process of claim 7 wherein the etherate is the reaction product of the ether and boron trifluoride reacted in a mole ratio of at least about 1:1.

9. The process of claim 4 wherein $R_1$ is isopropyl.

10. The process of claim 9 wherein the etherate is the reaction product of the ether and boron trifluoride reacted in a mole ratio of at least about 1:1.

* * * * *